United States Patent

Van Wijngaarden et al.

[11] Patent Number: 5,223,625
[45] Date of Patent: Jun. 29, 1993

[54] ANNELATED INDOLO [3,2,-C]LACTAMS

[75] Inventors: Ineke Van Wijngaarden; Hans H. Haeck; Derk Hamminga; Wouter Wouters, all of Weesp, Netherlands

[73] Assignee: Duphar International Research B.V., Weesp, Netherlands

[21] Appl. No.: 913,901

[22] Filed: Jul. 16, 1992

Related U.S. Application Data

[62] Division of Ser. No. 452,501, Dec. 19, 1989, abandoned.

[30] Foreign Application Priority Data

Dec. 22, 1988 [NL] Netherlands ............... 8803135

[51] Int. Cl.[5] ............................. C07D 519/00
[52] U.S. Cl. .................... 546/70; 540/579; 540/581; 540/582; 544/14
[58] Field of Search ............. 546/70; 514/288

[56] References Cited

U.S. PATENT DOCUMENTS

| | | | |
|---|---|---|---|
| 3,299,078 | 1/1967 | Pachter et al. | 546/67 |
| 3,914,421 | 10/1975 | Rajagopalan | 424/248 |
| 4,939,136 | 7/1990 | Haeck et al. | 514/183 |
| 4,985,420 | 1/1991 | Hamminga et al. | 514/211 |
| 4,997,831 | 3/1991 | Bays et al. | 514/211 |

FOREIGN PATENT DOCUMENTS

| | | |
|---|---|---|
| 0297651 | 1/1989 | European Pat. Off. |
| 0306323 | 3/1989 | European Pat. Off. |
| 0322016 | 6/1989 | European Pat. Off. |
| 0327307 | 8/1989 | European Pat. Off. |
| 3740352 | 6/1988 | Fed. Rep. of Germany |
| 2153821 | 8/1985 | United Kingdom |

OTHER PUBLICATIONS

Uyeo et al., Chemical Abstracts, vol. 61, No. 10725a (1964).
Dahlgren et al., Chemical Abstracts, vol. 99, (1983), No. 70652g.

Primary Examiner—Nicholas S. Rizzo
Assistant Examiner—Philip I. Datlow
Attorney, Agent, or Firm—Stevens, Davis, Miller & Mosher

[57] ABSTRACT

The invention relates to a group of new annelated indolo [3,2-c] lactam derivatives of the formula

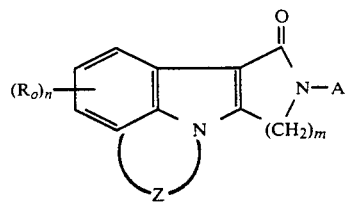

having an antagonistic activity on 5-HT receptors. The compounds can be used for the treatment of symptoms which are caused by excessive stimulation of said receptors in the gastrointestinal system, the central nervous system, the cardiovascular system, the respiratory system, and for alleviating or preventing withdrawal symptoms which are induced by abuse of drugs.

2 Claims, No Drawings

ANNELATED INDOLO [3,2,-C]LACTAMS

This is a division of application Ser. No. 07/452,501, filed Dec. 19, 1989, now abandoned.

The invention relates to new heterocyclic compounds having an antagonistic activity on 5-hydroxytryptamine (5-HT) receptors, to the preparation thereof and to pharmaceutical compositions which comprise such a new compound as an active substance.

Britisch Patent Specification no. 2153821 relates to heterocyclic compounds having an antagonistic activity on 5-HT receptors. These known compounds have the general formula 1

$$\text{(1)}$$

wherein $R_1'$ is hydrogen, alkyl, alkenyl, cycloalkyl, cycloalkylalkyl, phenyl or phenylalkyl, and Im is an optionally substituted imidazole radical.

It has been found surprisingly that compounds of the formula 2

$$\text{(2)}$$

wherein $R_0$ is alkyl, alkoxy or alkylthio having 1-4 C-atoms, hydroxy, halogen, a group $R_1R_2N$ or $R_1R_2-N-CO$, wherein $R_1$ and $R_2$ are hydrogen or alkyl having 1-4 C-atoms or wherein $R_1R_2N$ is a saturated 5-6 ring, n has the value 0, 1 or 2, m has the value 1-4, Z, together with the carbon atom and the nitrogen atom and the intermediate carbon atom, constitutes a hereocyclic group which consists of 5-8 ring atoms and wherein besides the nitrogen atom already present, a second hetero atom from the group N, O, S, S—O or $SO_2$ may be present, which ring may be substituted with 1-4 alkyl groups having 1-4 C-atoms, a phenyl group or a spiroalkkyl group ($C_{2-5}$), or which ring may be annelated with a saturated or non-saturated carbocyclic or heterocyclic ring which consists of 5- or 6-ring atoms and which may be substituted, A is a group of formula 3 or 4, $$\text{(3)}$$

$$\text{(4)}$$

wherein one of the groups $R_3$, $R_4$ and $R_5$ is hydrogen, alkyl having 1-6 C-atoms, cycloalkyl having 3-7 C-atoms, alkenyl having 2-6 C-atoms or phenylalkyl having 1-3 C-atoms in the alkyl group, and the two other groups independently of each other are hydrogen or alkyl having 1-4 C-atoms, or wherein A represents a polycarbocyclic group, for example of the formula 5,6 or 7 wherein one carbon atom is replaced by a tertiary nitrogen atom $$\text{(5)}$$

$$\text{(6)}$$

$$\text{(7)}$$

in which groups p has the value 1 or 2, q is 2,3 or 4, r is 1,2 or 3, and $R_6$ is alkyl having 1-4 C-atoms, cycloalkyl having 3-6 C-atoms, cyclopropylmethyl, allyl, propargyl or benzyl, and the pharmaceutically acceptable acid addition salts thereof have a similar but considerably prolonged activity and a lower toxicity than the known compounds of formula 1.

Suitable acids with which the compounds of formula 2 according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaaric acid, acetic acid, benzoic acid, p-toluene sulphonic acid, methane sulphonic acid, and the like.

One or more chiral centre(s) can be present in the compounds having formula 2. The invention includes both the racemates and the individual enantiomers of compounds of formula 2.

The antagonistic activity of the compounds of formula 2 on the 5-HT-induced response was determined and measured in the von Bezold-Jarisch reflex test in rats. The affinity to "neuronal" 5-HT receptors was determined and measured by the displacement of ($^3$H)GR 38032F of neuroblastoma cells.

On the basis of the antagonistic activity of this type of 5-HT receptors the compounds may be used for the treatment of symptoms which are caused by excessive stimulation of the said receptors a) in the gastrointestinal system (nausea and vomitting as a result of exogenous factors, for example, cancer therapy, or endogenous factors, for example, stasis of the stomach and migraine), ulcer, dyspepsia, spasms, irritable bowel syndrome, etc., or b) in the central nervous system (hallucinations, delusions, manias, fear, depression, pain, improvement of the vigilance, etc.), or c) in the cardiovascular system, for example, spasms of the vessels, arrhythmia, etc., or d) in the respiratory system (including nasal disturbances and disturbances of bronchi and lungs, or e) for alleviating or preventing withdrawal symptoms which are induced by abuse of drugs.

The compounds according to the invention and their salts may be brought into forms suitable for administration, for example, pills, tablets, coated tablets, capsules, powders, injection liquids and the like, by means of techniques conventionally used for this purpose and while using suitable auxiliary substances, for example, solid or liquid carrier materials.

The dosage in which the compounds according to the invention may be used depends on the severity and the nature of the disease to be treated and on the mode of administration. As a rule the dosage will be between 0.05 and 20 mg, preferably between 0.1 and 10 mg of active substance daily.

The compounds of formula 2, wherein $R_0$, Z, n, m, and A have the above-mentioned meanings may be prepared according to at least one of the following manners. i) Compounds having formula 2 wherein A is a group of the formula 3 or 4 can be obtained by reaction of a compound of formula 8

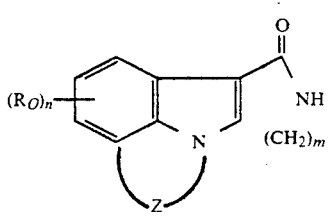

(8)

wherein $R_0$, Z, n and m have the above-mentioned meanings with a compound of formula 9 or 10

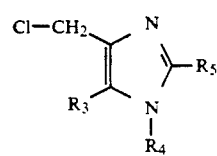

(9)

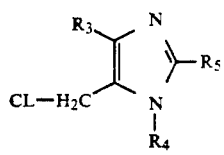

(10)

wherein $R_3$, $R_4$ and $R_5$ have the above mentioned meaning, on the understanding that $R_4$ cannot be hydrogen, or wherein $R_4$ may be triphenylmethyl, in the presence of potassium hydroxide, preferably in a solvent, for example, dimethyl sulphoxide, dimethyl formamide, etc., optionally succeeded by splitting off the triphenylmethyl group in acid conditions, for example in a mixture of acetic acid and water.

The starting compounds of formula 8 required for these reactions may be prepared a) by Beckmann reaction of the corresponding compounds of formula 11

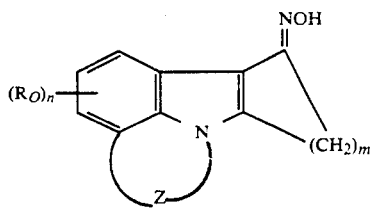

(11)

The compounds of formula 11, may be prepared in a manner known per se from the analogous ketones having formula 12

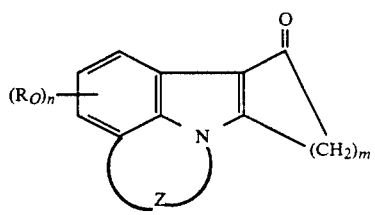

(12)

with hydroxylamine. The compounds having formula 12 may be prepared in a manner known for analogous compounds, for example, by oxidation of a compound of formula 13

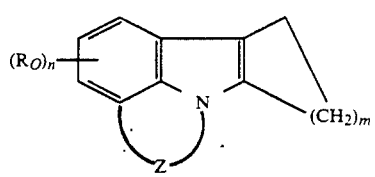

(13)

wherein $R_0$, n, m and Z have the meanings mentioned in formula 2 with a suitable oxidation agent, for example, 2,3-dichloro-5,6-dicyano-1,4-benzoquinone (DDQ) or selenium dioxide, preferably in a suitable solvent, for example, water, tetrahydrofuran or dioxan. In particular, the compounds having formula 12 can be obtained in a good yield by oxidation with DDQ of the analogous compounds of formula 13 in tetrahydrofuran and water at temperatures between $-10°$ and $20°$ C., as described for similar compounds in J. Org. Chem. 42 (1977), p. 1213. The compounds of formula 13 are known compounds or can be obtained in a manner analogous to known compounds.

Further the starting substances of formula 12 can be obtained by Fisher-indole ring closure of compounds of formula 14.

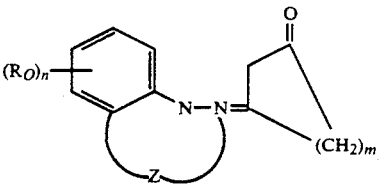

(14)

wherein $R_0$, Z, n and m have the meanings mentioned in formula 2.

These ring closure reactions may be carried out by boiling in an organic solvent, for example, acetic acid in the presence of an acid catalyst, for example, concentrated hydrochloric acid or sulphuric acid.

The compounds of formula 14 may be obtained analogously to known compounds, for example, by reaction of a compound of formula 15

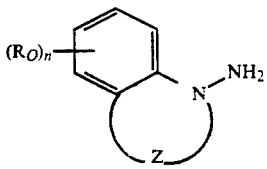
(15)

with a compound of formula 16

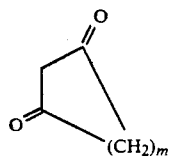
(16)

The compounds of formulae 15 and 16 are known compounds or can be obtained analogously to known compounds.

b) The starting compounds having formula 8 can also be obtained by Fischer-indole ring closure of a compound of formula 17

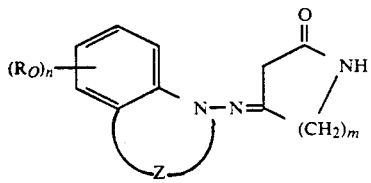
(17)

wherein $R_0$, Z, n and m have the meanings mentioned in formula 2.

These ring closure reactions may be carried out in an organic solvent, for example ethylene glycol or acetic acid, optionally in the presence of an acid catalyst, for example, hydrochloric acid or sulphuric acid, at temperatures between 50° and 225° C. More particularly, this ring closure may be carried out without a catalyst, giving a good yield, in ethylene glycol at temperatures between 150° and 210° C.

The compounds of formula 17 used as starting compounds for these reactions can be obtained analogously to known compounds, for example, by reacting a compound of formula 15 with compound of formula 18

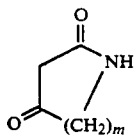
(18)

The starting compounds of formula 18 required for this reaction are known compounds or can be prepared analogously to known compounds. Good methods of preparation for the compounds of formula 18 are described in Heterocycles 13 (1979), 477–495.

The starting compounds of formulae 9 and 10 used in method i) for the preparation of compounds having formula 2 according to the invention are known compounds or can be obtained analogously to known compounds.

ii) Compounds of formula 2 can also be prepared by reacting a compound of formula 19

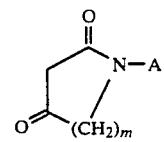
(19)

wherein A and m have the above meaning, with a compound of formula 15, wherein $R_0$, n and Z have the above meaning, followed by Fischer-indole ring closure of the obtained product. This ring closure reaction may be carried out in an organic solvent, for example, ethylene glycol or acetic acid, if desired in the presence of an acid catalyst, for example, hydrochloric acid or sulphuric acid, at temperatures between 50° and 225° C. Preferably the reaction is carried out without a catalyst in ethylene glycol at 150°–210° C.

The starting compounds of formula 19 can be obtained in the same manner as compounds of formula 18.

iii) Compounds of formula 2 wherein A is a group of formula 3 or 4, on the understanding that $R_4$ is not hydrogen, can also be prepared by metalation of a compound of formula 2 wherein $R_0$, A, n, m and Z have the above-mentioned meanings, with the proviso that $R_4$ in formulae 3 and 4 represents a hydrogen atom, and subsequent reaction of the formed metal compound with a compound of the formula $R_4$-X wherein X is a group which may be replaced by a nucleophile, for example, a halogen atom. The reaction is preferably carried out in a solvent, for example, dimethylformamide, ethanol, dimethyl sulphoxide, with metalation reagents, for example, sodium hydride, potassium tertiary butoxide, sodium ethanolate, etc.

The starting compounds of formula 2 required for the said metalation can be obtained, for example, by means of the above methods of preparation described sub i) and ii).

The invention will now be described in greater detail with reference to the ensuing specific examples.

EXAMPLE I

11-[(5-methyl-1H-imidazol-4-yl)methyl]-4,5,6,7,9,10,11,12octahydro-pyrido[3',4':4,5]pyrrolo[3,2,1-jk][1]benzazepin12-one.

a) 1 g of potassium hydroxide was added to 10 ml of dimethylsulphoxide, and the mixture was stirred for 5 minutes. 0.72 g (3 mmol) of 4,5,6,7,9,10,11,12-octahydropyrido[3',4':4,5]pyrrolo[3,2,1-jk][1]benzazepin-12-one were added, and the mixture was warmed at 40° C. 2.5 g (6.7 mmol) of the mixture of isomers of 1-triphenylmethyl-4 (or 5)-chloromethyl-5 (or 4)-methylimidazole were added, and the mixture was stirred for 30 minutes at 40° C. Another 0.5 g of the mixture of isomers was added, and stirring at 40° C. was continued for 1 hour. The mixture was poured on ice-water. The solid material was sucked off, dried and chromatographed over silica gel using methylene chloride/methanol (95/5) as an eluent. After evaporating the desired fractions 2.0 g of 11-[(5(or 4)-methyl-1-triphenylmethyl-imidazol-4(or 5)-yl)methyl]-4,5,6,7,9,10,11,12octahydro-pyrido[3',4':4,5]pyrrolo[3,2,1-jk][1]benzazepin12-one were obtained.

b) The product obtained in a) above was boiled for 1 hour in a mixture of 40 ml of acetic acid and 40 ml of water. After cooling the solid material was sucked off. The filtrate was diluted with 40 ml 50% sodium hydroxide while cooling, and shaken with methylene chloride containing 10% of methanol. The methylene chloride-methanol solution was evaporated, and the residue was chromatographed over silica gel using methylene chloride/methanol (9:1) as an eluent. After evaporating the desired fractions 0.67 g of the title compound were obtained. Melting point 224°-226° C. C-13 NMR (SLV: CDCl₃, Ref: TMS, ADT: Me OH)

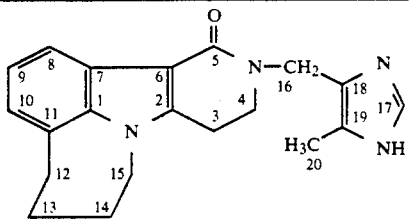

| 1 | 137.39 S | 8 | 123.00 D * | 15 | 45.57 T |
|---|---|---|---|---|---|
| 2 | 143.96 S | 9 | 118.34 D | 16 | 40.12 T |
| 3 | 22.02 T | 10 | 121.88 D * | 17 | 133.91 D |
| 4 | 45.96 T | 11 | 126.86 S # | 18 | 131.80 |
| 5 | 166.01 S | 12 | 28.21 T + | 19 | 125.06 |
| 6 | 105.78 S | 13 | 26.84 T + | 20 | 11.36 Q |
| 7 | 126.42 S # | 14 | 32.64 T | | |

BROAD LINES FOR C-ATOMS 18 AND 19

In the same manner were obtained:
1) 10-{(5-methyl-1H-imidazol-4-yl)methyl}-5,6,8,9,10,11-hexahydro-4H-pyrido[3',4':4,5]pyrrolo[3,2,1-ij]quinolin-11-one; melting point 226°-228° C. (decomposition). C-13-NMR (SLV: CDCl₃, Ref.: TMS)

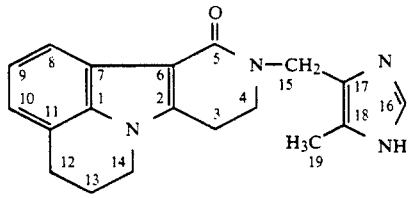

| 1 | 134.49 S | 8 | 121.86 D # | 15 | 40.33 T * |
|---|---|---|---|---|---|
| 2 | 142.34 S | 9 | 117.94 D # | 16 | 133.75 D |
| 3 | 21.20 T | 10 | 119.55 D # | 17 | 131.19 S |
| 4 | 46.10 T * | 11 | 123.45 S | 18 | 125.58 S |
| 5 | 166.09 S | 12 | 24.49 T | 19 | 11.29 Q |
| 6 | 105.42 S | 13 | 22.47 T | | |
| 7 | 121.63 S | 14 | 41.70 T | | |

2. 11-{(5-methyl-1H-imidazol-4-yl)methyl}-5,6,9,10,11,12-hexahydro-4H, 8H-azepino[3',4':4,5] pyrrolo[3,2,1-ij]quinolin-12-one; melting point 215°-216° C. C-13-NMR (SLV: CDCl₃, Ref.: TMS, ADT: MeOH)

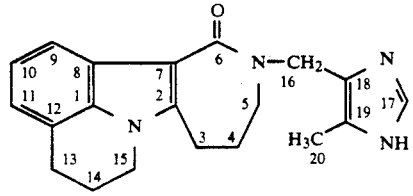

| 1 | 133.81 S | 8 | 126.42 S | 15 | 41.80 T # |
|---|---|---|---|---|---|
| 2 | 140.72 S | 9 | 119.39 D | 16 | 42.45 T # |

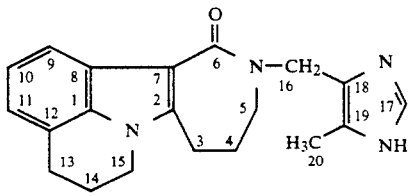

| 3 | 26.09 T * | 10 | 121.38 D | 17 | 133.81 D |
|---|---|---|---|---|---|
| 4 | 25.79 T * | 11 | 119.56 D | 18 | 130.94 S |
| 5 | 47.47 T | 12 | 121.02 S | 19 | 125.89 S |
| 6 | 167.94 S | 13 | 24.40 T | 20 | 11.16 Q |
| 7 | 107.13 S | 14 | 22.66 T | | |

LINES OF C-ATOMS 18 AND 19 ARE BROAD

12-{(5-methyl-1H-imidazol-4-yl)methyl}-4,5,6,7,10,11,12,13-octahydro-9H-azepino[3',4';4,5]pyrrolo[3,2,1-jk][1]benzazepin-13-one; melting point 215°-217° C. C-13-NMR (SLV: CDCl₃, Ref.: TMS)

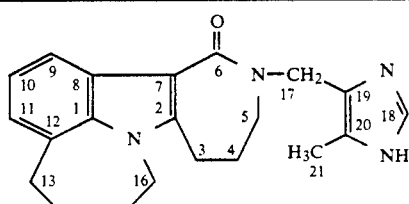

| 1 | 136.86 S | 8 | 128.52 S # | 15 | 31.64 T |
|---|---|---|---|---|---|
| 2 | 141.33 S | 9 | 122.85 D * | 16 | 44.34 T |
| 3 | 26.48 T + | 10 | 119.62 D | 17 | 42.98 T |
| 4 | 26.31 T + | 11 | 121.24 D * | 18 | 133.65 D |
| 5 | 47.75 T | 12 | 126.17 S # | 19 | 131.63 |
| 6 | 167.97 S | 13 | 28.11 T + | 20 | 125.51 |
| 7 | 108.10 S | 14 | 26.93 T + | 21 | 11.68 Q |

LINES OF C-ATOMS 19 AND 20 ARE VERY BROAD.

EXAMPLE II

8-{(4-methyl-1H-imidazol-5-yl)methyl}-1,2,7,8,9,10-hexahydro-pyrido[3',4';4,5]pyrrolo[1,2,3-de][1,4]benzothiazin-7-one 0.6 g (3.6 mmol) of 4-amino-3,4-dihydro-2H-[1,4]benzothiazine and 0.75 g (3.6 mmol) of 1-(4-methylimidazol-5-yl)methyl-2,4-diketopiperidine were boiled for 2 hours in 10 ml of absolute ethanol. The mixture was evaporated in vacuo, 15 ml of ethylene glycol were added to the residue, the mixture was stirred for 1.5 hours at 175° C., cooled, diluted with water and shaken with methylene chloride. The methylene chloride solution was washed and evaporated in vacuo. The residue was chromatographed over 180 ml of silica gel using methylene chloride/methanol (9:1) as an eluent. After evaporating the desired fractions and stirring the residue in warm ethyl acetate 0.32 g of the title compound were obtained. Melting point 223°-225° C. (decomposition)

C-13-NMR (SLV: DMSO, Ref.: TMS)

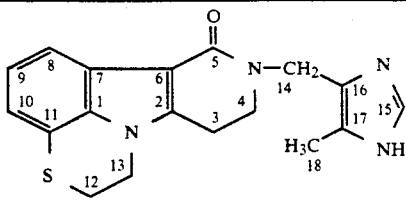

| | | | | | |
|---|---|---|---|---|---|
| 1 | 130.43 S | 7 | 124.20 S | 13 | 42.72 T |
| 2 | 143.76 S | 8 | 121.45 D # | 14 | 39.76 T |
| 3 | 20.53 T | 9 | 118.12 D # | 15 | 133.19 D |
| 4 | 44.86 T | 10 | 116.52 D # | 16 | *.00 |
| 5 | 163.38 S | 11 | 116.84 S | 17 | *.00 |
| 6 | 104.87 S | 12 | 25.25 T | 18 | 9.96 Q |

LINES OF C-ATOMS 16 AND 17 ARE NOT SHOWN (VERY BROAD)

In the same manner were obtained: 3-{(4-methyl-1H-imidazol-5-yl)methyl}-1,2,3,4,8,9-hexahydro-pyrido[4',3':2,3]indolo[1,7a,7-ab][1]benzazepin-4-one; melting point 217°–220° C. (decomposition) C-13-NMR (SLV: CDCl₃, Ref.: TMS)

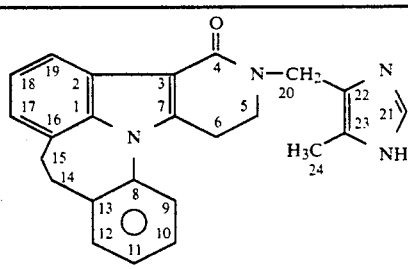

| | | | | | |
|---|---|---|---|---|---|
| 1 | 137.01 S + | 9 | 124.35 D * | 17 | 122.02 D # |
| 2 | 126.40 S | 10 | 126.60 D * | 18 | 118.43 D # |
| 3 | 109.42 S | 11 | 126.37 D * | 19 | 123.85 D * |
| 4 | 165.57 S | 12 | 130.24 D | 20 | 40.42 T |
| 5 | 46.75 T | 13 | 135.87 S + | 21 | 133.86 D |
| 6 | 24.71 T | 14 | 34.39 T | 22 | *.00 |
| 7 | 142.87 S | 15 | 34.36 T | 23 | *.00 |
| 8 | 137.27 S + | 16 | 127.32 S | 24 | 11.54 Q |

LINES OF C-ATOMS 22 AND 23 ARE NOT SHOWN (VERY BROAD)

EXAMPLE III 8-(1-azabicyclo[2,2,2]oct-3-yl)-1,2,7,8,9,10-hexahydro-pyrido[3',4';4,5]pyrrolo[1,2,3-de][1,4]benzothiazin-7-one.

a) N-(1-azabicyclo[2,2,2]-oct-3-yl)-β-alanine ethyl ester 0.92 g (20 mmol) of sodium were dissolved in 100 ml of ethanol. 4.0 g (20 mmol) of 3-amino-quinuclidine dihydrochloride were added and the mixture was stirred for 5 minutes. 2 g (20 mmol) of ethyl acrylate were added, the mixture was boiled for 20 hours, and evaporated in vacuo. The residue was shaken with little water and methylene chloride. The organic layer was separated and evaporated in vacuo, giving 3.1. g of the desired product.

b) N-ethoxycarbonylethyl, N-(1-azabicyclo[2,2,2-,]oct-3-yl)-β-alanine ethyl ester.

The product obtained in a) above (13.5 mmol) was dissolved in 30 ml of acetonitrile. A solution of 1.81 g (13.7 mmol) of malonic acid mono-ethyl ester in 10 ml of acetonitrile and a solution of 2.86 g (13.7 mmol) of cyclohexylcarbodiimide in 10 ml of acetonitrile respectively were added dropwise. The mixture was stirred for 3 hours at room temperature, the solid material was sucked off and the filtrate was evaporated in vacuo. The residue was chromatographed over silica gel using methylene chloride/methanol/ammonia (85/14/1) as an eluent. After evaporating the desired fractions 2.85 g of the desired product were obtained as an oil.

c) 8-(1-azabicyclo[2,2,2]oct-3-yl)-1,2,7,8,9,10-hexahydro-pyrido[3',4';4,5]pyrrolo[1,2,3-de][1,4]benzothiazin-7-one.

1.0 g (2.95 mmol) of the product of b) was added to the reaction mixture of 0.07 g (3.05 mmol) of sodium and 25 ml of methanol, the mixture was boiled for 20 hours, and evaporated in vacuo. The residue was suspended in 30 ml of acetonitrile and 0.25 ml (2.95 mmol) of concentrated hydrochloric acid were added while stirring, the mixture was boiled for 2 hours while stirring, and evaporated in vacuo. After addition of acetonitrile the mixture was evaporated once more. The so-obtained crude 1-(1-azabicyclo[2,2,2]oct-3-yl)-2,4-diketopiperidine was boiled for 2 hours together with 0.45 g (5.9 mmol) of ammonium acetate and 0.5 g (2.95 mmol) of 4-amino-3,4-dihydro-2H-1,4-benzothiazine in 25 ml of absolute ethanol. The obtained residue after evaporating in vacuo was shaken with methylene chloride and water, the methylene chloride layer was separated and evaporated in vacuo. The residue was chromatographed over silica gel using methylene chloride/methanol/ammonia (85/14/1) as an eluent. After evaporating the desired fractions 0.6 g of the desired hydrazone was obtained as a foam. This product (1.62 mmol) was dissolved in 15 ml of ethylene glycol and stirred for 45 minutes under nitrogen at 175° C. The solvent was removed by distillation in vacuo, the residue was shaken with water and methylene chloride, the organic layer was separated and evaporated in vacuo. The residue was chromatographed over silical gel using methylene chloride/methanol/ammonia (85/14/1) as an eluent. After evaporating the desired fractions 0.38 g of the desired product were obtained as a foam. C-13-NMR (SLV: CDCl₃, Ref.: TMS)

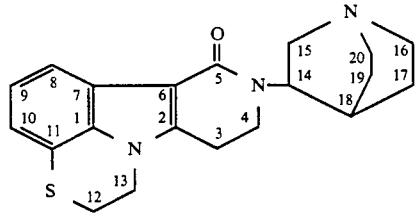

| | | | | | |
|---|---|---|---|---|---|
| 1 | 131.11 S | 8 | 117.82 D | 15 | 51.87 T |
| 2 | 142.33 S | 9 | 122.40 D | 16 | 47.41 T # |
| 3 | 21.70 T | 10 | 119.34 D | 17 | 27.94 T * |
| 4 | 43.28 T | 11 | 116.60 S | 18 | 26.48 D |
| 5 | 165.65 S | 12 | 25.94 T | 19 | 22.22 T * |
| 6 | 106.88 S | 13 | 42.85 T | 20 | 46.82 T # |
| 7 | 124.82 S | 14 | 49.36 D | | |

In the same manner were obtained;

1) 10-(1-azabicyclo[2,2,2]oct-3-yl)-5,6,8,9,10,11-hexahydro-4H-pyrido[3',4':4,5]pyrrolo[3,2,1-ij]quinolin-11-one (foam) C-13-NMR (SLV: CDCl₃, Ref.: TMS)

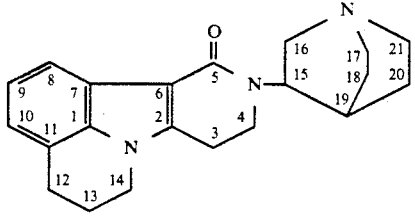

| 1 | 134.59 S | 8 | 118.17 D | 15 | 49.28 D |
| 2 | 142.16 S | 9 | 121.85 D | 16 | 51.94 T |
| 3 | 21.41 T | 10 | 119.58 D | 17 | 47.41 T # |
| 4 | 43.26 T | 11 | 121.66 S | 18 | 27.49 T * |
| 5 | 166.22 S | 12 | 24.49 T | 19 | 26.33 D |
| 6 | 106.34 S | 13 | 22.56 T | 20 | 22.22 T * |
| 7 | 123.70 S | 14 | 41.86 T | 21 | 46.84 T # |

2) 10-(1-azabicyclo[2,2,2]oct-3-yl)-2-fluoro-5,6,8,9,10,11-hexahydro-4H-pyrido[3',4':4,5]pyrrolo[3,2,1-ij]quinolin-11-one (foam) C-13-NMR (SLV: CDCl$_3$, Ref.: TMS)

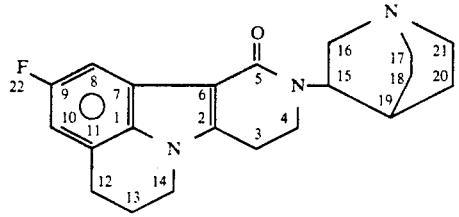

| 1 | 130.95 S | 8 | 103.26 D | 15 | 49.43 D |
| 2 | 143.15 S | 9 | 159.32 S | 16 | 52.11 T |
| 3 | 21.64 T | 10 | 107.82 D | 17 | 47.42 T # |
| 4 | 41.66 T | 11 | 122.84 S | 18 | 28.02 T * |
| 5 | 165.89 S | 12 | 24.38 T | 19 | 26.38 D |
| 6 | 106.39 S | 13 | 22.36 T | 20 | 22.11 T * |
| 7 | 123.73 S | 14 | 42.97 T | 21 | 46.82 T # |

Coupling Constants:

| J(9, F22) = 235.4 | J(10, F22) = 26.2 | J(8, F22) = 25.4 |
| J(7, F22) = 11.6 | J(11, F22) = 10.2 | J(6, F22) = 5.1 |

3) 3-(1-azabicyclo[2,2,2]oct-3-yl)-1,2,3,4,8,9-hexahydro-pyrido[4',3':2,3]indolo[1,7a,7-ab][1]benzazepin-4-one C-13-NMR (SLV: CDCl$_3$, Ref.: TMS)

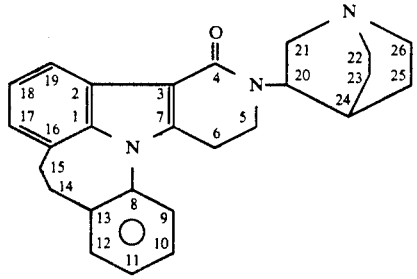

| 1 | 137.35 S | 10 | 126.65 D * | 19 | 123.85 D * |
| 2 | 126.68 S | 11 | 126.32 D * | 20 | 49.47 D |
| 3 | 110.56 | 12 | 130.38 D | 21 | 52.10 |
| 4 | 165.70 | 13 | 135.95 S | 22 | 47.70 T + |
| 5 | 43.59 T | 14 | 34.50 T | 23 | 28.34 T & |
| 6 | 21.95 T | 15 | 34.38 T | 24 | 26.61 D |
| 7 | 142.47 | 16 | 127.02 S | 25 | 25.76 & |
| 8 | 137.35 S | 17 | 121.92 D # | 26 | 47.07 T + |
| 9 | 124.39 D * | 18 | 118.78 D # | | |

LINES OF C-ATOMS 3 4 5 6 7 13 AND QUINUCLIDINE-RING ARE BROAD.

4) 11-(1-azabicyclo[2,2,2]oct-3-yl)-4,5,6,7,9,10,11,12-octahydro-pyrido[3',4':4,5]pyrrolo[3,2,1-jk][1]benzazepin-12-one (foam) C-13-NMR (SLV: CDCl$_3$, Ref.; TMS)

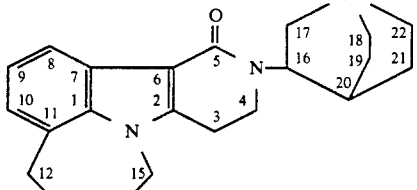

| 1 | 137.45 S | 9 | 118.74 D | 17 | 51.82 T |
| 2 | 143.58 S | 10 | 121.82 D * | 18 | 47.45 T + |
| 3 | 21.57 T | 11 | 126.71 S # | 19 | 27.68 T & |
| 4 | 43.01 T | 12 | 28.34 T = | 20 | 26.43 D |
| 5 | 165.93 S | 13 | 26.93 T = | 21 | 23.10 T & |
| 6 | 106.96 S | 14 | 32.78 T | 22 | 46.87 T + |
| 7 | 126.63 S # | 15 | 45.74 T | | |
| 8 | 122.98 D * | 16 | 49.13 D | | |

5) 10-(endo-8-methyl-8-azabicyclo[3,2,1]oct-3-yl)-5,6,8,9,10,11-hexahydro-4H-pyrido[3',4':4,5]pyrrolo[3,2,1-ij]quinolin-11-one C-13-NMR (SLV: CDCl$_3$, Ref.: TMS)

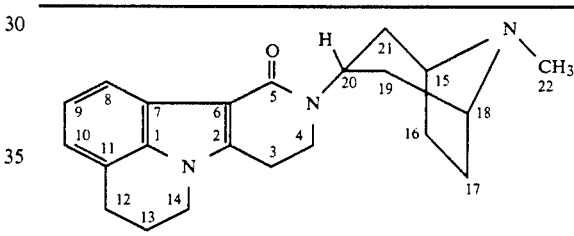

| 1 | 134.38 S | 9 | 121.30 D | 17 | 29.30 T |
| 2 | 141.90 S | 10 | 119.10 D | 18 | 58.98 D |
| 3 | 21.64 T | 11 | 121.50 S | 19 | 34.92 T |
| 4 | 42.38 T | 12 | 24.38 T | 20 | 42.64 D |
| 5 | 165.03 S | 13 | 22.40 T | 21 | 34.92 T |
| 6 | 106.29 S | 14 | 41.56 T | 22 | 40.52 Q |
| 7 | 123.56 S | 15 | 58.98 D | | |
| 8 | 118.02 D | 16 | 29.30 T | | |

6) 11-(endo-8-methyl-8-azabicyclo[3,2,1]oct-3-yl)-4,5,6,7,9,10,11,12-octahydro-pyrido[3',4':4,5]pyrrolo[3,2,1-jk][1]benzazepin-12-one C-13-NMR (SLV: CDCl$_3$, Ref.: TMS)

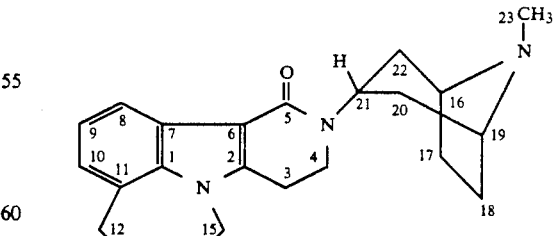

| 1 | 137.25 S | 9 | 118.59 D | 17 | 29.41 T |
| 2 | 143.47 S | 10 | 121.30 D * | 18 | 29.41 T |
| 3 | 22.56 T + | 11 | 126.63 S # | 19 | 58.93 D |
| 4 | 42.19 T | 12 | 28.22 T + | 20 | 34.98 T |
| 5 | 164.82 S | 13 | 26.87 T | 21 | 42.63 D |
| 6 | 106.89 S | 14 | 32.73 T | 22 | 34.98 T |
| 7 | 126.48 S # | 15 | 45.49 T | 23 | 40.55 Q |

-continued

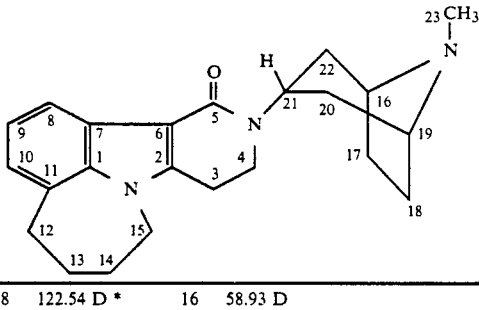

| 8 | 122.54 D * | 16 | 58.93 D |

Preparation of intermediates a) 5,6,9,10,11,12-hexahydro-4H,8H-azepino[3',4':4,5-]pyrrolo[3,2,1-ij]quinolin-12-one 11.8 g (49 mmol) of 11-oximino-5,6,8,9,10,11-hexahydro-4H-pyrido-[3,2,1-jk]carbazole, obtained in the usual manner from the corresponding ketone, were added to 200 g of polyphosphoric acid of 90° C. The mixture was then stirred for 30 minutes at 130° C., cooled to 100° C., poured on ice, and stirred until a black mass has formed. The water layer was separated and the residue was stirred for 24 hours with a mixture of 150 ml of 2N lye, 200 ml of methylene chloride and 50 ml of alcohol. The methylene chloride layer was then separated, dried and evaporated. The residue was chromatographed over 400 g of silica gel using methylene chloride/2% methanol as an eluent. After evaporating the desired fractions, 5.0 g (42%) of the desired product were obtained. Melting point 280°-282° C. (decomposition).

In the same manner the following compound was obtained:
4,5,6,7,10,11,12,13-octahydro-9H-azepino[3',4':4,5-]pyrrolo[3,2,1-jk][1]benzazepin-13-one; melting point 247°-249° C.

b) 4,5,6,7,9,10,11,12-octahydro-pyrido[3',4':4,5]pyrrolo[3,2,1-jk][1]benzazepin-12-one.

1.6 g (10 mmol) of 1-amino-2,3,4,5-tetrahydro-1H-[1]benzazepine and 1.1 g (10 mmol) of 2,4-diketopiperidine were added to 10 ml of ethanol. The mixture was boiled for 1 hour and evaporated in vacuo. 20 ml of ethylene glycol were added to the residue and the mixture was stirred for 5 hours at 175° C. under an atmosphere of nitrogen. 50 ml of water were added after cooling, while stirring. After sucking off and drying 1.8 g of crude product were obtained, which was chromatographed over silica gel using methylene chloride/methanol (95/5) as an eluent. After evaporating the desired fractions 1.2 g of the title compound were obtained. Melting point 225°-226° C.

In the same manner the following compounds were prepared:

1) 1,2,3,4,8,9-hexahydro-pyrido[4',3':2,3]indolo[1,7a,7-a,b][1]benzazepin-4-one; melting point 243°-244° C.

2) 2,3,7,8-tetrahydro-1H-pyrrolo[3',4':2,3]indolo[1,7a,7-a,b][1]benzazepin-3-one; melting point 130°-132° C. (decomposition)

3) 5,6,9,10-tetrahydro-4H,8H-pyrrolo[3',4':4,5]pyrrolo[3,2,1-ij]quinolin-10-one; melting point 255° C. (slow decomposition)

4) 1,2,8,9-tetrahydro-7H-pyrrolo[3',4':4,5]pyrrolo[1,2,3-de][1,4]benzothiazin-7-one; melting point 260°-265° C. (decomposition)

5) 5,6,8,9,10,11-hexahydro-4H-pyrido[3',4':4,5]pyrrolo[3,2,1-ij]quinolin-11-one; melting point 251°-252° C.

c) 1-(4-methyl-imidazol-5-yl)methyl-2,4-diketopiperdine i) N-{(1-triphenylmethyl-4[or 5]methyl-1H-imidazol-5[or 4]-yl)methyl}-β-alanine ethyl ester 1.1 ml (10.1 mmol) of ethyl acrylate were added to a solution of 3.8 g (11 mmol) of the mixture of {(1-triphenylmethyl-4-methyl-1H-imidazol-5-yl)methyl}amine and {(1-triphenylmethyl-5-methyl-1H-imidazol-4-yl)methyl}amine in 40 ml of absolute ethanol at 0° C., and the mixture was stirred overnight. The temperature raised to 20° C. The mixture was evaporated in vacuo and the residue was chromatographed over silica gel using methylene chloride/methanol (9/1) as an eluent. 4.25 g of product (pale yellow oil) were obtained after evaporating the desired fractions.

ii) N-(ethoxycarbonyl-acetyl),N-{(1-triphenylmethyl-4(or 5)methyl-1H-imidazol-5(or 4)-yl)methyl}-β-alanine ethyl ester.

The product of i) (9.4 mmol) was dissolved in 30 ml of methylene chloride and cooled at 0° C. At this temperature a solution of 1.25 g (9.4 mmol) of the monoethyl ester of malonic acid in 10 ml of methylene chloride were added dropwise. Subsequently a solution of 1.25 g (9.5 mmol) of dicyclohexylcarbodiimide in 10 ml of methylene chloride was added. The solid material was sucked off after stirring for 3 hours. The filtrate was evaporated in vacuo. 5.3 g of the desired product (as a yellow oil which crystallised slowly) was obtained.

iii) 1-(4-methyl-imidazol-5-yl)methyl-2,4-diketopiperidine

The product of ii) was dissolved in 150 ml of toluene. The obtained solution was added to the reaction mixture of 0.22 g (9.5 mmol) of sodium and 15 ml of methanol. The mixture was boiled for 6 hours and evaporated in vacuo. The residue was dissolved in 23 ml of water of 0° C. 1.25 ml of concentrated hydrochloric acid were added while cooling with ice-water. The mixture was saturated with NaCl and shaken with methylene chloride. The organic layer was washed with brine, dried and evaporated in vacuo. The residue was suspended in a mixture of 46 ml of acetonitrile and 4.5 ml of water, boiled for 1 hour and evaporated in vacuo. The residue was stirred with 65 ml of ether. The solid material was sucked off and washed with ether. 1.9 g of the desired product (melting point 140° C., decomposition) were obtained.

We claim:
1. A compound having the formula:

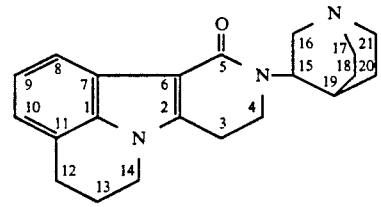

2. A compound having the formula:

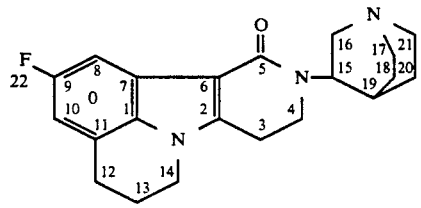

* * * * *